US009706723B2

(12) United States Patent
Arnold et al.

(10) Patent No.: US 9,706,723 B2
(45) Date of Patent: Jul. 18, 2017

(54) METHODS FOR CREATING DOUBLED HAPLOID MAIZE EMBRYOS USING OIL MATRICES

(71) Applicant: PIONEER HI-BRED INTERNATIONAL INC, Johnston, IA (US)

(72) Inventors: Randal Arnold, Ankeny, IA (US); Roberto Barreiro, Honolulu, HI (US); Matthew Paul Cope, Johnston, IA (US); Clifford P Hunter, Mililani, HI (US); Justin Andrew Schares, Ames, IA (US); Xinli Emily Wu, Johnston, IA (US); Yue Yun, Johnston, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 0 days.

(21) Appl. No.: 14/793,689

(22) Filed: Jul. 7, 2015

(65) Prior Publication Data
US 2017/0006766 A1    Jan. 12, 2017

Related U.S. Application Data

(63) Continuation-in-part of application No. 14/473,183, filed on Aug. 29, 2014, now Pat. No. 9,078,427, which is a continuation-in-part of application No. 14/473,114, filed on Aug. 29, 2014.

(51) Int. Cl.
*A01H 1/08* (2006.01)
*A01C 1/02* (2006.01)
*C12Q 1/68* (2006.01)
*A01G 1/00* (2006.01)
*C12N 15/82* (2006.01)

(52) U.S. Cl.
CPC ............... *A01H 1/08* (2013.01); *A01C 1/025* (2013.01); *A01G 1/001* (2013.01); *C12N 15/8205* (2013.01); *C12Q 1/6895* (2013.01)

(58) Field of Classification Search
None
See application file for complete search history.

(56) References Cited

U.S. PATENT DOCUMENTS

| | | | |
|---|---|---|---|
| 5,138,793 A * | 8/1992 | Florin | A01H 4/00 435/1.1 |
| 8,119,342 B2 | 2/2012 | Van Dun | |
| 8,404,930 B2 | 3/2013 | Wu et al. | |
| 8,859,846 B2 | 10/2014 | Barton et al. | |
| 8,865,971 B2 | 10/2014 | Zhao et al. | |
| 2008/0216191 A1* | 9/2008 | Barton | A01H 1/08 800/276 |
| 2009/0215060 A1 | 8/2009 | Deppermann et al. | |
| 2013/0210006 A1 | 8/2013 | Rapier et al. | |

FOREIGN PATENT DOCUMENTS

| | | |
|---|---|---|
| WO | 02/085014 A2 | 10/2002 |
| WO | WO-02/085104 A2 * | 10/2002 |
| WO | 2012/011091 A2 | 1/2012 |
| WO | WO-2012/011091 A2 * | 1/2012 |
| WO | 2013/119962 A1 | 8/2013 |
| WO | 2013/182646 A1 | 12/2013 |
| WO | 2014/071271 A1 | 5/2014 |

OTHER PUBLICATIONS

McKently et al (Plant Cell Reports (1995) 14:699-703).*
Yamakawa et al (Agric. Bioi. Chem (1983) 47: 2185-2191).*
King et al (Biotechnology (1989) 7:1037-1042).*
Palumbi et al, Simple Fool's Guide to PCR version 2.0 (2002), University of Hawaii.*
Horn and Rafalski 1992 (Plant Molecular Biology Reporter 10:3 p. 285-293).*
Sylvie Antoine-Michard et al., Spontaneous versus colchicine-induced chromosome doubling in maize anther culture, Plant Cell, Tissue and Organ Culture, 1997, pp. 203-297, vol. 48.
A Kato, Maize Genetics Cooperation Newsletter, 1997. pp. 36-37.
Y Wan et al., Efficient production of doubled haploid plants through colchicine treatment of anther-derived maize callus, Theor Appl Genet, 1989, pp. 889-892, vol. 77.
Y Wan et al., The use of antimicrotubule herbicides for the production of doubled haploid plants from anther-derived maize callus, Theor Appl Genet, 1991, pp. 205-211, vol. 81.
Peggy Horn et al., Non-Destructive RAPD Genetic Diagnostics of Microspore-Derived Brassica Embryos, Plant Molecular Biology Reporter, 1992, pp. 285-293, vol. 10(3).
International Search Report—PCT/US2015/039449—Mailed Oct. 7, 2015.

* cited by examiner

*Primary Examiner* — Matthew Keogh

(57) ABSTRACT

Methods for preserving viability of plant tissues such as plant embryos are provided herein. Also included are methods for storing genomic DNA and/or molecular marker assay materials in an oil bilayer as part of a high-throughput molecular characterization system. Moreover, plant embryos may be treated while in an oil matrix. The treatment may include chromosome doubling, *Agrobacterium*-mediated transformation, or herbicide selection as part of an embryo rescue process.

2 Claims, No Drawings

METHODS FOR CREATING DOUBLED HAPLOID MAIZE EMBRYOS USING OIL MATRICES

CROSS REFERENCE TO RELATED APPLICATIONS

This application is a continuation-in-part of U.S. National application Ser. No. 14/473,183, filed Aug. 29, 2014, and a continuation-in-part of U.S. National application Ser. No. 14/473,114, filed Aug. 29, 2014, which are incorporated by reference in their entirety.

BACKGROUND

Present conventional seed analysis methods used in genetic, biochemical, or phenotypic analysis, require at least a part of the seed to be removed and processed. In removing some seed tissue, various objectives may need to be met. These may include one or more of the following objectives:

(a) maintain seed viability after collection of seed tissue, if required, (b) obtain at least a minimum required amount of tissue, without affecting viability, (c) obtain tissue from a specific location on the seed, often requiring the ability to orient the seed in a specific position, (d) maintain a particular throughput level for efficiency purposes, (e) reduce or virtually eliminate contamination, and (f) allow for the tracking of separate tissues and their correlation to seeds from which the tissues were obtained.

Current conventional seed testing technologies do not address these requirements sufficiently, resulting in pressures on capital and labor resources, and thus illustrate a need in the art to provide seed analysis methods in which the maximum number of objectives is realized. It would also be beneficial if the seed analysis methods could be used in conjunction with other methods in the seed production process.

SUMMARY

Methods for storing, treating and selecting plant embryos are provided herein. Methods for storing genomic DNA and molecular marker assay materials in an oil bilayer for use in high-throughput molecular analysis are also provided. Moreover, methods for treating plant embryos while in an oil matrix are provided, the treatment of which may be chromosome doubling, *Agrobacterium*-mediated transformation, or herbicide selection as part of an embryo rescue process.

In some embodiments, plant embryos may be stored by suspending the plant embryos or plant embryonic tissue in an aqueous solution surrounded by a matrix of one or more oils. Preferably, at least one of the one or more oils has a density greater than that of the aqueous solution. In some aspects, antimicrobial agents and/or minimal growth media may be added to the aqueous solution. In other aspects, the plant embryos or plant embryonic tissue may be stored in cold (preferably 4° C.) and/or dark conditions to prevent premature germination. In some embodiments, the plant embryos or plant embryonic tissue may be transferred for continued storage. In other embodiments, the plant embryos may be transferred to germination medium, and one or more of the plant embryos may be germinated. In still other embodiments, an aliquot of the aqueous solution may be removed, genetic material may be obtained from cellular material in the aliquot, and the genetic material may be used for molecular analysis (e.g. to genotype the stored plant embryos). The molecular analysis may be genotyping, which may occur by way of: single nucleotide polymorphism detection, restriction fragment length polymorphism identification, random amplified polymorphic detection, amplified fragment length polymorphism detection, polymerase chain reaction, DNA sequencing, whole genome sequencing, allele specific oligonucleotide probes, or DNA hybridization to DNA microarrays or beads. In other embodiments, one or more of the steps described above may be automated.

In some embodiments, methods of storing genomic DNA are provided in which genomic DNA, immersed in an aqueous solution, is placed between two oils, one being more dense than water and the other being less dense than water. The genomic DNA in between the oil layers may be stored under light or dark conditions. The genomic DNA in between the oil layers may be stored at a temperature between room temperature and approximately −25 degrees Celsius, or preferably at approximately −20 degrees Celsius. The methods may further comprise removing an aliquot of said genomic DNA as part of an automated process to perform a molecular analysis such as but not limited to genotyping.

In some embodiments, methods of storing molecular marker assay materials, immersed in an aqueous solution, are provided in which genomic DNA is placed between two oils, one being more dense than water and the other being less dense than water. Molecular marker assay materials may comprise primers and probes. The molecular marker assay materials located between the oil layers may be stored under light or dark conditions. The molecular marker assay materials located between the oil layers may be stored at a temperature between room temperature and −25 degrees Celsius. The methods may further comprise removing an aliquot of said molecular marker assay materials as part of an automated process to perform a molecular analysis such as but not limited to genotyping.

In some embodiments, methods of treating plant embryos with a doubling agent are provided. The methods comprise placing doubling media in between two oils, wherein one of the oils is more dense than water and the other is less dense than water; placing one or more plant embryos in the doubling media for 8-48 hours under light conditions; selecting plant embryos; and transferring the selected plant embryos to media for germination or storage. The plant embryos may be haploid. Moreover, an aliquot of the media may be removed, genetic material may be obtained from cellular material in the aliquot, and the genetic material may be used for molecular analysis (e.g. to genotype the treated plant embryos). The molecular analysis may be genotyping, In some embodiments, methods of selecting plant embryos during doubled haploid production are provided. In the methods, (a) doubling media is placed between two oils, in which one of the oils is more dense than water and the other is less dense than water; (b) the plant embryos are placed in the doubling media for 8-48 hours under light conditions, and (c) plant embryos are selected for germination or storage. Between steps (b) and (c), cellular material may be collected from the one or more plant embryos; DNA may be obtained from the cellular material; and genotypic information may be obtained, allowing selection of one or more embryos based on genotypic information. The methods may further comprise transferring the selected plant embryos to media for germination or storage. The doubling media may comprise an anti-microtubule agent. The doubling media may comprise colchicine, pronamide, dithipyr, amiprophosmethyl or trifluralin. The plant embryos placed in the doubling media may be haploid.

In some embodiments, the plant embryos are maize haploid embryos produced by a cross between a male inducer line and a female line of interest, in which the male inducer line contains a marker gene that is expressed in embryo tissue. The marker gene may express anthocyanin pigments, which are only expressed in the diploid embryos. Thus, white embryos that do not express anthocyanin may further be selected for transfer to media for germination or storage. The selection may be performed using a camera or other imaging device. The methods may further comprise germinating or storing the selected embryos.

To facilitate selection of the white embryos, the expression of anthocyanin may be enhanced by aeration of the doubling media or by placing the plant embryos in a hypotonic doubling media comprising perfluorodecalin (PFC).

In some embodiments, methods of transforming plant tissue are provided in which a suspension comprising *Agrobacterium tumefaciens*, which comprises within its genome a recombinant DNA construct comprising one or more genes of interest and a selectable marker gene, between two oils, in which one oil is more dense than water and the other is less dense than water; placing the plant tissue in the suspension; removing the plant tissue from said suspension and cultivating the plant tissue in media; resting the plant tissue in media; and placing the plant tissue in contact with media comprising a selection agent corresponding to the selectable marker gene. The method may further comprise regenerating a plant from said plant tissue, wherein said plant tissue is a plant embryo or plant callus. The plant tissue may be stored in said suspension for up to one hour. Step (d) may comprise resting the plant tissue in media in the dark at a temperature of about 28 degrees Celsius for a period of up to 14 days. The media comprising the selection agent corresponding to the selectable marker gene may be located between two oils, wherein one of the oils is more dense than water and the other is less dense than water.

In some embodiments, methods of incubating plant tissue in a solution comprising a selection agent are provided in which the plant tissue in said solution is located between two oils, wherein one of the oils is more dense than water and the other is less dense than water. The selection agent may be glyphosate, glufosinate, bialaphos, hygromycin B, kanamycin, paromomycin, mannose, phosphinothricin, butafenacil, or R-haloxyfop. The method may further include selecting plant tissue that remains viable following incubation. The plant tissue may be a plant embryo or plant callus.

DETAILED DESCRIPTION

Plant breeding programs can benefit from preservation of viable plant sources, which may include keeping the viable plant sources in a manner that preserves an ability to be grown into a plant as well as keeping the viable plant sources in a manner that prevents germination. One benefit can be seen in that genetic material can be obtained for molecular characterization, allowing selections to be made prior to growing the plant. Additional benefits may include treating haploid plant embryos with chromosome doubling agents while being preserved or transforming viable plant sources while being preserved.

Viable plant sources may be seeds, plant embryos, plant tissue, or whole plants. Most typically, viable plant sources are capable of being grown into plants, although not necessarily. Preservation of seeds typically requires no particular care. When the viable plant sources are embryos, however, special care should be taken to preserve viability.

In one preferred method, plant embryos are suspended in an aqueous solution surrounded by a matrix of one or more oils. Oil having a density less than water will cover the plant embryo(s) in the aqueous solution, while oil having a density greater than water will support the plant embryo(s) in the aqueous solution. In some embodiments, the one or more plant embryos is suspended in an aqueous solution surrounded by a matrix of two or more oils, wherein at least one of the two or more oils is more dense than the aqueous solution and at least one of the two or more oils is less dense than the aqueous solution, further wherein the aqueous solution is surrounded by the oil that is more dense than the aqueous solution and the oil that is less dense than the aqueous solution. In some embodiments, antimicrobial agents and/or minimal growth media may be added to the aqueous solution. In some embodiments, the plant embryos may be stored in cold and/or dark conditions to prevent premature germination. In a preferred embodiment, the plant embryos are stored at a temperature of approximately 4° C. In some embodiments, the plant embryos may be transferred for continued storage. In other embodiments, the plant embryos may be transferred to germination medium, and the plant embryos may be germinated. In a preferred embodiment, an aliquot of the aqueous solution may be removed; genetic material may be obtained from cellular material in the aliquot; and the genetic material may be used for molecular analysis (e.g. to genotype the stored plant embryos).

High density oil that may be used in this method includes but is not limited to perfluoro compounds having 12 compounds (e.g., DuPont's lower viscosity KRYTOX® oils). Low density oil that may be used in this method includes but is not limited to phenylmethylpolysiloxane. Other non-toxic oils known to those of ordinary skill in the art may be used instead of or in combination with these compounds.

Obtaining Genetic Material for Molecular Characterization

In order for genetic material to be analyzed, it must be freed from the cell such that it is accessible for molecular analysis. This may involve physical treatments such as exposure to cold-heat or just heat, incubation with enzymes, or even DNA extraction techniques (although it is important to note that extraction is not a necessary step in obtaining DNA for molecular analysis). Essentially any process that disrupts the tissue and breaks open cells, thereby releasing DNA that can be used for molecular characterization, may be used in the methods provided herein.

In some embodiments, DNA may be obtained from the cellular material by exposing the cellular material to cold-heat or heat, agitating the mixture, and optionally repeating. In other embodiments, DNA may be obtained by incubating cellular material with an enzyme; the enzyme may be VISCOZYME® L, a multi-enzyme complex containing a wide range of carbohydrases, including arabanase, cellulase, β-glucanase, hemicellulase, and xylanase. (See the Sigma Aldrich product catalog). In still other embodiments, obtaining DNA may comprise extraction of the DNA, such as through the use of magnetic particles that bind genetic material or any method known to one of ordinary skill in the art. However, extraction is not necessary for obtaining DNA.

Molecularly Characterizing the Genetic Material from the Multiple Viable Plant Sources In cases where the yield of DNA obtained from embryo tissue is not sufficient for some molecular analysis (e.g. high density genotyping), whole genome amplification techniques may be used. The Qiagen REPLI-g kit, the Sigma- Aldrich SeqPlex kit, or any other technique known to one of ordinary skill in the art may be used to amplify DNA from plant embryonic tissue.

Other useful molecular characterizations may involve sequencing all or part of the genome of the tissue extracted from the seed, or using molecular markers and fluorescent probes to genotype. Molecular characterization need not focus on the genotype of the extracted tissue, but instead may measure other properties such as oil content, oil composition, protein content, or the presence or absence of particular molecules in the tissue.

In a preferred embodiment, genetic material is placed in a well of a multiple well plate containing a bilayer of oil, one layer having a density greater than water and one layer having a density less than water. Multiple wells contain multiple different genetic materials. Fluorescently labeled probes are added to the genetic materials, and thermocycling to cause amplification and hybridization of the probes is performed in the multiple well plate. The wells are irradiated and fluorescence is detected from the labels to generate genotypic data. Alternatively, the genetic material may be sequenced, in whole or in part, in the multiple well plate.

Genomic DNA and/or molecular marker assay materials (such as but not limited to primers and probes) may also be stored in a bilayer of oil to facilitate automation and high-throughput molecular characterization. In both instances, the materials are immersed in an aqueous solution, which is placed between two oils, one being more dense than water and the other being less dense than water. Storage of genomic DNA and/or molecular marker assay materials may be in light or dark conditions and may occur at approximately 4 degrees Celsius or at room temperature. Storage in this manner allows a mechanical device to obtain aliquots from stored genomic DNA and from stored molecular marker assay materials and combine them in a reaction mixture in order to perform high-throughput molecular characterization.

Selecting One or More Viable Plant Sources

In a molecular breeding program, plants or potential plants are selected to participate in subsequent generations based on their genotype. Typically this involves determining whether the plant has inherited one or more desirable traits indicated by genetic markers whose presence or absence can be determined based on the genotyping. Plant breeders select those plants that have the desired traits to participate in further breeding, to inbreed, or as part of a process to create inbreds through haploid doubling techniques. Those plants that are selected based on the presence of desirable traits as determined by their genotype may be grown into mature plants, to obtain haploid material to create a double haploid inbred, to breed with itself to create an inbred, or to breed with other plants to improve and diversify germplasm.

The plant embryo storage methods described above allow genotypic information to be obtained for plant embryos that are being stored, allowing embryos to be selected based on genotypic information.

The plant embryo storage methods may also be used to treat plant embryos while the plant embryos are stored (short-term or long-term) in an oil matrix.

One treatment may be the doubling of plant embryos with a doubling agent. In the methods, doubling media is placed between two oils, wherein one of the oils is more dense than water and the other is less dense then water; the plant embryos are placed in doubling media for 8-48 hours under light conditions; plant embryos are selected; and the selected plant embryos are transferred to media for germination or storage. The plant embryos may further be germinated or stored. The plant embryos may be haploid. Genetic material may be obtained from the plant embryos and the plant embryos may be molecularly characterized (e.g. genotyping). Selections of the plant embryos may be based on genotypic information.

Methods of chromosome doubling in maize are disclosed in Antoine-Michard, S. et al., *Plant cell, tissue organ cult.*, Cordrecht, the Netherlands, Kluwer Academic Publishers, 1997, 48(3):203-207; Kato, A., *Maize Genetics Cooperation Newsletter* 1997, 36-37; Wan, Y. et al., *TAG*, 1989, 77: 889-892. Wan, Y. et al., *TAG*, 1991, 81: 205-211; U.S. Pat. No. 8,865,971; and U.S. Pat. No. 8,404,930; the disclosures of which are incorporated herein by reference. Typical methods involve contacting the cells with colchicine, anti-microtubule agents or anti-microtubule herbicides, pronamide, nitrous oxide, or any mitotic inhibitor to create homozygous doubled haploid cells. The amount of colchicine used in medium is generally 0.01%-0.2% or approximately 0.05% or APM (5-225 µM). The amount of colchicine can range from approximately 100-600 mg/L, and preferably may be approximately 500 mg/L. The amount of pronamide in medium is approximately 0.5-20 µM. Other agents may be used with the mitotic inhibitors to improve doubling efficiency. Such agents may be dimethyl sulfoxide (DMSO), adjuvants, surfactants, and the like.

In some embodiments, methods of selecting plant embryos during doubled haploid production are provided. In the methods, (a) doubling media is placed between two oils, in which one of the oils is more dense than water and the other is less dense than water; (b) the plant embryos are placed in the doubling media for 8-48 hours under light conditions, and (c) plant embryos are selected. Between steps (b) and (c), cellular material may be collected from the one or more plant embryos; DNA may be obtained from the cellular material; and genotypic information may be obtained, allowing selection of one or more embryos based on genotypic information. The methods may further comprise transferring the selected plant embryos to media for germination or storage and/or germinating the plant embryos. The doubling media may comprise an anti-microtubule agent. The doubling media may comprise colchicine, pronamide, dithipyr, amiprophosmethyl or trifluralin. The plant embryos placed in the doubling media may be haploid.

Maize haploid embryos may be produced by a cross between a male inducer line and a female line of interest, in which the male inducer line contains a marker gene that is expressed in embryo tissue. The marker gene may express anthocyanin pigments, which are only expressed in the diploid embryos. Thus, white embryos that do not express anthocyanin may further be selected for transfer to media for germination or storage. The selection may be performed using a camera or other imaging device.

In the above, expression of anthocyanin (or the observation thereof) may be enhanced by aeration of the doubling media. This may occur by shaking the liquid media prior to contact with the plant embryos or by bubbling filtered air through the three layers (first oil layer, liquid medium, second oil layer) since the phase separation would occur once the air supply is shut down. Another method involves placing the plant embryos in a hypotonic doubling media comprising perfluorodecalin (PFC). The hypotonic doubling media may also comprise bleach to reduce bacterial growth.

The female line of interest may or may not be an inbred and may have a desirable genetic makeup. The female line of interest may also comprise within its genome one or more transgenes of interest.

The haploid inducer lines described herein have incorporated anthocyanin color markers incorporated into their genomes; the markers are expressed both within the kernel pericarp and in the scutellum. The color markers are used to screen the embryos. Haploid embryos lack the paternal gene with the color marker and therefore appear white or colorless.

One of the limitations of using liquid media is that the color marker fails to be expressed when the embryos are submerged in the medium and therefore it is difficult to separate diploids from haploids embryos after doubling. To overcome this limitation, methods to increase dissolved oxygen content within the media may be used to enhance the level of anthocyanin expression or the observation thereof. In methods described herein, anthocyanin expression in liquid media may be enhanced by incubating the embryos in hypotonic liquid media consisting of perfluorodecalin (PFC), a liquid saturated in oxygen, and 0.1% commercial bleach (5% NaOCl v/v), by shaking, and/or by bubbling the medium with filtered air (aeration). Enhancement of anthocyanin expression in liquid media may be performed while the liquid media is located between oils in an oil matrix; however, it is not necessary for the liquid media to be between oils. Selection is facilitated whether or not the liquid media is located between oils in an oil matrix. Moreover, the use of the hypotonic doubling media comprising perfluorodecalin (PFC) to enhance anthocyanin expression is not exclusive to liquid media and may be used to eliminate diploid embryos regardless of how the plant embryos are being stored.

Another treatment may be the transformation of plant tissue with *Agrobacterium tumefaciens*, which has within its genome a recombinant DNA construct that comprises one or more genes of interest and a selectable marker gene. The methods include placing a suspension containing the *Agrobacterium* between two oils, in which one oil is more dense than water and the other is less dense than water; placing the plant tissue in the suspension; removing the plant tissue from the suspension and cultivating the plant tissue in media; resting the plant tissue in the media; and placing the plant tissue in contact with media comprising a selection agent corresponding to the selectable marker gene. The method may further comprise regenerating a plant from said plant tissue, which may be a plant embryo or plant callus. The plant tissue may be stored in the suspension for up to one hour. "Resting" may comprise placing the plant tissue in media in the dark at a temperature of about 28 degrees Celsius for a period of up to 14 days. The media comprising the selection agent may also be located between two oils, wherein one of the oils is more dense than water and the other is less dense than water. However, the step of selecting the embryos can also be performed in media that is not located within an oil matrix.

The benefits to performing *Agrobacterium*-mediated transformation of embryos in an oil matrix are simplification of the downstream multiple culturing process, amenability for automation, a reduction in costs pertaining to consumables, and a reduction in consumable waste.

Another treatment may be the incubation of plant tissue in a solution containing a selection agent. This also may be done while the plant tissue is located between two oils, wherein one of the oils is more dense than water and the other is less dense than water. The selection agent may be glyphosate, glufosinate, bialaphos, hygromycin B, kanamycin, paromomycin, mannose, phosphinothricin, butafenacil, or R-haloxyfop. The method may further include selecting plant tissue that remains viable following incubation. The plant tissue may be a plant embryo or plant callus. This method may be used to determine whether plant tissue includes a native trait that confers the ability to withstand the selection agent.

While the examples provided herein relate to a monocot, specifically maize, those of ordinary skill in the art would understand how to apply the same or similar methods to other monocots and dicots; the methods may be adapted to any plant. For instance, the plant may include but is not limited to maize, soybean, sunflower, sorghum, canola, wheat, alfalfa, cotton, rice, barley, millet, sugar cane, or switchgrass.

Example 1: Embryo Genotyping in Maize

A. Collection of Maize Embryo Material:

Maize embryos were washed 3 times using 2 mL of sterile water. Maize embryos were incubated in a tube containing either 10 µL, 20 µL, 50 µL, 75 µL, or 150 µL of sterile water for either 10 minutes, 20 minutes, or overnight. It was found that adequate genotyping data can be obtained with any of the dilution volumes, and that 10 minutes was a sufficient incubation time. All protocols for washing and incubating the maize embryos were used with all three tissue collection methods described below.

Method 1: The tubes containing the maize embryos were agitated via tapping 10 times and were then spun down in a tabletop centrifuge for 5 seconds. The water was then removed from each tube for analysis. It was found that this method achieved the best results for genotyping.

Method 2: Maize embryos were washed 3 times using 2 mL of sterile water. The maize embryos were incubated in a tube containing 50 µL of sterile water for 10 minutes. The water was then removed from the tube for analysis.

Method 3: Maize embryos were washed 3 times using 2 mL of sterile water. The maize embryos were incubated in a tube containing 50 µL of sterile water for 10 minutes. Tubes containing the maize embryos were agitated via tapping 10 times. The water was then removed from each tube for analysis.

B. Methods to Obtain DNA:

Cold-Heat Shock:

Maize embryonic material obtained using all three methods described above was placed in a −80° C. freezer for 20 min; then placed on a thermocycler at 100° C. for 10 min and pipetted up and down to mix. The process was repeated for a total of two rounds. The resulting mixtures were stored at −20° C. It was found that the best results for genotyping were achieved from DNA obtained using this method.

Heat Shock Only:

Maize embryonic tissues were placed on a thermocycler at 100° C. for 10 min and pipetted up and down to mix. The process was repeated for a total of two rounds. The mixtures were stored at −20° C.

Enzymatic Method:

The mixtures from the preceding step were incubated in a 95° C. oven to evaporate off the remaining water. 18.0 µL of PBS solution and 2.0 µL of diluted VISCOZYME® L (commercially available from Sigma-Aldrich; diluted 1:200 in PBS Solution pH 7.4; total vol. 20 µL) were added and the mixtures were incubate at 37° C. for 2 hours. A quantity of 2.0 µL of diluted proteinase K (commercially available from Sigma-Aldrich; diluted 1:20 in PBS Solution pH 7.4) was added and the mixtures were incubated at 55° C. for 50 minutes then heated to 95° C. for 10 min. The mixtures were stored at −20° C.

DNA Extraction:

The mixtures from the methods of Example 1B were incubated in a 95° C. oven to evaporate off the remaining water. 45 µL Lysis buffer PN (LGC Genomics) was added to each mixture, each of which was centrifuged briefly and incubated at 65° C. for 1 hour. To new tubes were added 60 µL Binding buffer PN, 5 µL Sbeadex particles (magnetic particles that bind genetic material, which are commercially available from LGC Genomics) followed by the lysate mixtures, which were then incubated at room temperature for 4 minutes to allow binding of DNA to the particles, vortexed briefly and placed in a magnetic rack to concentrate beads. The lysis buffer was removed and 100 µL wash buffer PN1 (LGC Genomics) was added to resuspend the beads. Washing was repeated using 100 µL wash buffer PN2 (LGC Genomics) followed by a 100 µL pure water wash. 10 µL elution buffer PN was added and the mixtures were incubated at 55° C. for 10 minutes with vortexing every 3 minutes. The magnetic rack was used to concentrate beads and the eluate was transferred to new tubes and stored at −20° C.

C. Whole Genome Amplification

When whole genome amplification was required the following protocol was followed using the REPLI-g®Single Cell Kit (commercially available from Qiagen). Whole genome amplification was done to achieve higher DNA yield and to facilitate the detection of high density marker sets.

2.5 µL template DNA was combined with 2.5 µL Buffer D1 (commercially available from Qiagen; total volume 5.0 µL) and incubated at room temperature for 3 minutes. 5.0 µL Buffer N1 (commercially available from Qiagen; total volume 10.0 µL) was added and the mixtures were vortexed and centrifuged briefly. A Master Mix containing 9.0 µL nuclease-free water, 29.0 µL REPLI-g® Reaction Buffer (commercially available from Qiagen) and 2.0 µL REPLI-g® DNA Polymerase (commercially available from Qiagen) was used per reaction to give 50.0 µL total volume. The mixtures were run on a thermocycler using a 30° C. for 8 hours and 4° C. thereafter. DNA quantitation was performed using a Qubit assay (commercially available from Life Technologies). The DNA product was used directly in the genotyping step.

D. Molecular Analysis

TAQMAN® Marker Analysis

Marker analysis was carried out using TAQMAN® assays (commercially available from Life Technologies). DNA was diluted to a target concentration of 20 ng/µL. A 384 plate containing the DNA was loaded into LC480 real-time PCR thermocycler and run using the following program: pre-incubation: 1 cycle (95° C. for 5 minutes); amplification: 45 cycles, (−95° C. for 30 seconds, −60° C. for 45 seconds (single acquisition), −72° C. for 1 minute (single acquisition); cooling: 1 cycle, (−72° C. for 10 minutes, −40° C. for 30 seconds). Calls were read using Roche LC480 LightCycler® Software (commercially available from Roche Diagnostics).

Results

The foregoing methods all gave acceptable genotyping results.

Example 2: Maize Embryo Storage

Two lines of maize germplasm were selected for testing the impacts of extended embryo storage in an oil matrix on germination rates. Embryos from each line were isolated by hand before being placed into their respective storage condition. All embryos were plated on germination media to evaluate germination rates in a controlled growth chamber. Six embryos of each line were immediately plated on germination media without any storage exposure to act as a control for germination in a controlled growth chamber. Seventy two (72) embryos of each line were isolated and evenly divided across three storage conditions, with a dedicated storage tube for each embryo:

Storage condition 1: 24 embryos were placed in 50 µL aqueous solution surrounded by two layers of oil with significantly different densities, one with a density significantly greater than water and one with a density significantly less than water.

Storage condition 2: 24 embryos were placed in a 50 uL droplet of aqueous solution with an added antimicrobial agent, surrounded by the two oils of condition 1.

Storage condition 3: 24 embryos were placed in a 50 uL droplet of minimal growth media with an added antimicrobial agent, surrounded by the two oils of condition 1.

All tubes were placed in a dark refrigerator at 4 degrees centigrade for the duration of the experiment. At four (4) time points, 6 embryos of each line were removed from their storage condition and plated on germination media in a controlled growth chamber to evaluate germination rates. The time points were as follows:

Time point 1: 15 minutes after placement into storage.
Time point 2: 1 day after placement into storage.
Time point 3: 5 days after placement into storage.
Time point 4: 10 days after placement into storage.

Embryo germination rates were then monitored to determine optimal storage conditions. It was found that germination rates were excellent for embryos stored in each of the three storage methods.

Example 3: Genotyping Reagent Storage Study Methods and Materials

Two components of an endpoint SNP genotyping reaction, genomic DNA and a molecular marker assay (primers and probe), were selected to test the impacts on reagent viability after extended storage in an oil bilayer, at various conditions.

Genomic DNA was isolated from maize leaf tissue and from maize seed tissue via known extraction protocols to evaluate the impact of extended storage, compared to a baseline. A volumetric subset from each tissue type extraction was left at stock extraction concentration and the remaining volume was diluted to a factor well suited for a SNP genotyping reaction. The DNA concentration volumes were further divided to provide dedicated volumes for evaluating storage impacts in Light vs. Dark conditions and Room Temperature vs. 4° Celsius conditions, as well as a combination of each.

Four molecular marker assays used for endpoint SNP genotyping of maize were selected to evaluate impact of extended storage, compared to a baseline. A volumetric subset of each molecular marker assay was left at a stock concentration and the remaining volume of each molecular marker assay was diluted to a factor well suited for a SNP genotyping reaction. The molecular marker assay volumes were further divided to provide dedicated volumes for evaluating storage impacts in Light vs. Dark conditions and Room Temperature vs. 4° C. conditions, as well as a combination of each.

Prior to the volume separation steps, a baseline sample was taken from each reagent to generate a baseline data set for comparison at each storage time point. The extracted test DNA reagent was screened against a control molecular marker assay (not the test molecular marker assay) and the test molecular marker assays were screened against control DNA samples (not the test DNA samples). Each reagent volume was placed into an oil bilayer prior to being stored in their respective storage condition (Light/Dark, Room Temp/4° Celsius). At pre-defined time points, aliquots of reagents from each test storage condition, for each reaction component, were taken and screened against control reagent compliments within an endpoint SNP genotyping reaction. Genotypic data from all time points was compared to the baseline for reaction completion efficiency and overall data quality. Data quality from the stored molecular marker assay reagents was comparable to that of the baseline.

Example 4: Haploid Embryo Doubling and Selection in Oil Matrix

Experiments were performed to determine if doubling treatments can be applied to embryos stored in the oil bilayer.

2× colchicine selection media consisting of: 2×DCS Media (Doubling, Colchicine, Sucrose), 2×DCS Media components (per Liter), 300.00 g Sucrose Grade II, 8.67 g of MS Basal Salt Mixture, 0.80 g L-Asparagine Monohydrate, 10.00 mL 36J Vitamin Solution, 2.50 mL of Thiamine Solution, 0.20 mL of BAP Solution, 1.00 g Colchicine, 41.66 mL of DMSO (20%), and RO water to 1.00 L, was prepared. 2× colchicine selection media was placed in screw-top microcentrifuge tubes and diluted with an equal amount of sterile water to 1× concentration. 50 μL of 1× liquid colchicine selection media was added to each tube, which contained a high-density oil and a low-density encapsulating oil. The colchicine media settles between the oil layers.

Twenty embryos were rescued from an ear produced by a cross between a male inducer line, which comprises in its genome a marker gene that expresses anthocyanin pigments in embryo tissue, and a female line of interest. Embryos were transferred into the colchicine media using a sterilized spatula, and tubes were placed in a lighted growth chamber room for 8-48 hours. Embryos were selected based on the color image from a camera. Purple or diploid embryos were discarded, while the white embryos were transferred to growth media plates. The plates were then placed back in the culture chamber for germination. The germination rate for both haploid and diploid embryos is comparable to the standard protocol without using oil encapsulation.

Example 5: Enhancement of Anthocyanin Expression for Improved Selection

In the methods described in Example 5, the level of anthocyanin expression can be enhanced, resulting in improved selection. Either of the methods described below, as well as other methods known to one of ordinary skill in the art, may be used to increase dissolved oxygen content within the media, thereby enhancing the level of anthocyanin expression or the observation thereof.

In one experiment, the culture media was aerated prior to introducing the embryo into the oil matrix environment. Four mL of culture media in a 50 mL Falcon tube was prepared and placed in a rocker table at maximum speed for several hours. The media was immediately transferred into oil matrix tubes after aeration. The results indicate that the oxygen level in the medium facilitates the detection of anthocyanin coloration for the diploid embryos. Alternatively, liquid medium could also be aerated by bubbling filtered air through the three layers (first oil layer, liquid medium, second oil layer) since the phase separation would occur once the air supply is shut down.

In another experiment, embryos were incubated in a hypotonic liquid medium consisting of PFC (perfluorodecalin; undiluted and in whatever volume needed to cover the embryo) and 0.1% commercial bleach (5% NaOCl v/v). The addition of bleach was sufficient to inhibit bacterial growth without affecting germination when compared to the control. Anthocyanin color appeared at the border of the scutellum within 12 hours of the colchicine treatment and then continued centripetally until the whole embryo became purple-red (if diploid). Germination in liquid medium is statistically similar to the control using solid medium.

Example 6: *Agrobacterium*-mediated Transformation of Maize Embryos in an Oil Matrix An *Agrobacterium* suspension may be prepared (such as shown in U.S. Pat. No. 5,981,840) and then placed between two oils, one of which is more dense than water and the other of which is less dense than water. The *Agrobacterium*-containing suspension would settle between the oil layers.

Embryos are isolated and then placed in the *Agrobacterium*-containing suspension, which is located between the oil layers, for 5 minutes. The embryos are then removed from the *Agrobacterium*-containing suspension and then cultivated for 2-4 days. For the resting step, embryos are transferred to a new plate and incubated in the dark at approximately 28° C. for up to 14 days, in order to eliminate any remaining *Agrobacterium*. For selection, embryos are then placed in contact with media containing a selection agent that corresponds to the selectable marker gene inserted into the vector in the *Agrobacterium*, in order to kill any non-transformation events. The selection step can also take place in media located between two oils in an oil matrix. The transformed cells are then regenerated to form whole plants using tissue culture methods.

The benefit of allowing transformation of the embryo to occur while in media surrounded by the oil bilayer is to simplify the downstream multiple culturing process. The system is more automatable than the conventional methods transferring cultivates using agar based medium and would reduce the cost of consumables as well as the associated waste.

Example 7: Trait Selection of Maize Embryos in Oil Matrix

Effective selection is one of the most critical steps in selecting plants and plant tissues that contain a transgene or native trait of interest. The presence of a selecting agent allows for the proliferation of transgenic tissues and at the same time suppresses or kills untransformed tissue. Similarly, a selecting agent may be used to determine whether a plant tissue includes a native trait that confers the ability to withstand the selection agent. The ideal selection agent should not have a negative impact on subsequent regeneration, rooting and plant growth. Both antibiotics and herbicides can be used as selection agents. Commonly used agents include glyphosate, glufosinate, bialaphos, hygromycin B, kanamycin, paromomycin, mannose, phosphinothricin, butafenacil and R-haloxyfop.

Transformed plant tissue or plant tissue having a resistance trait, such as a plant embryo, can be placed in media comprised of MS salts 4.3 g/l; myo-inositol 0.1 g/l; Thiamine.HCL 0.1 mg/l, Pyridoxine.HCl 0.5 mg/l, Glycine 2.0 mg/l, nicotinic acid 0.5 mg/l and sucrose 40.0 g/l at a pH of 5.6. The selection agent can be added directly to such media and then the media containing the agent, along with the plant tissue, can be located between two oils, wherein one of the oils is more dense than water and the other is less dense than water.

Plant Embryos may be transferred into the selection-containing media using a sterilized spatula, and the embryos in the selection-containing media located between the two oils are placed at 8 degrees C. to 26 degrees C. for up to 7 days for selection. Only embryos that have within their genomes genes that confer tolerance to the selection agent will survive. Image selection based on morphological differences, for example by machine vision and computer processing, may be used to differentiate the viable embryos from the dead embryos.

We claim:

1. A method of treating one or more haploid maize embryos with a chromosome doubling agent, said method comprising:

a. placing chromosome doubling media between two oils, wherein one of the oils is more dense than water and the other is less dense than water;

b. placing one or more haploid maize embryos in the chromosome doubling media;

c. selecting one or more doubled haploid maize embryos; and d. transferring the selected doubled haploid maize embryos to media for germination or storage.

2. The method of claim 1, wherein between steps (c) and (d) cellular material is collected from the one or more doubled haploid maize embryos; DNA is obtained from the cellular material; genotypic information is obtained from the one or more doubled haploid maize embryos; and the doubled haploid maize embryos are selected based on the genotypic information.

* * * * *